(12) United States Patent
Wynne et al.

(10) Patent No.: US 7,189,867 B1
(45) Date of Patent: Mar. 13, 2007

(54) TRIFLUOROMETHYLCARBINOL TERMINATED THIOLS

(75) Inventors: James H Wynne, Alexandria, VA (US); Arthur W Snow, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/532,950

(22) Filed: Sep. 19, 2006

(51) Int. Cl.
*C07C 321/00* (2006.01)
*C07F 7/04* (2006.01)

(52) U.S. Cl. .................. 556/429; 556/113; 568/21; 568/62

(58) Field of Classification Search ................ 556/113, 556/429; 568/21, 62
See application file for complete search history.

(56) References Cited

U.S. PATENT DOCUMENTS

| 6,221,673 B1 | 4/2001 | Snow et al. |
| 2004/0181023 A1 | 9/2004 | Yamagishi et al. |

OTHER PUBLICATIONS

Andres et al., "Self-Assembly of a Two-Dimensional Superlattice of Molecularly Linked Metal Clusters", *Science*, 273, 1690-1693 (1998).
Bethell et al., "From Monolayers to Nanostructured Materials: an Organic Chemist's View of Self-Assembly", *J. Electroanal. Chem.*, 409, 137-143 (1996).
Brust et al., "Synthesis of Thiol-Derivatised Gold Nanoparticles in a Two-Phase Liquid-Liquid System", *J. Chem. Soc., Chem. Commun.*, 801-802 (1994).
Foos et al., "Synthesis and Characterization of Water-Soluble Gold Nanoclusters of Varied Core Size", *J. Cluster Sci.*, 13, 543-552 (2003).

Götzö et al., "EPC Syntheses of Trifluorocitronellol and of Hexafluoropyrenophorin—A Comparison of Their Physiological Properties with the Nonfluorinated Analogs", *Eur. J. Org. Chem.*, 1999, 2533-2544.
Grate et al., "Sorptive Behavior of Monolayer-Protected Gold Nanoparticle Films: Implications for Chemical Vapor Sensing", *Anal. Chem.* 2003, 75, 1868.
Hon et al., "Preparation of γ-Substituted Acroleins via the Reaction of Aldehyde or the Corresponding Ozonide with Dihalomethane and Diethylamine", *Tetrahedron* 1998, 54, 5233.
Krishnamurti et al., "Preparation of Trifluoromethyl and Other Perfluoroalkyl Compounds with (Perfluoroalkyl) trimethylsilanes", *J. Org. Chem.* 1991, 56, 984.
Nakamura et al., "Asymmetric Reduction of Trifluoromethyl Ketones Containing a Sulfur Functionality by the Alcohol Dehydrogenase from *Geotrichum*", *Tetrahedron*, 54, 8393-8402 (1998).
Snow et al., "Synthesis and Evaluation of Hexafluorodimethylcarbinol Functionalized Polymers as Microsensor Coatings", *J. Appl. Poly. Sci.* 43, 1659 (1991).
Urquhart et al., "n-Dodecyl (Lauryl) Mercaptan", *Org. Synth. Coll.* vol. III, 363 (1955).
Wohltjen et al., "Colloidal Metal-Insulator-Metal Ensemble Chemiresistor Sensor", *Anal. Chem.* 1998, 70, 2856.

*Primary Examiner*—Samuel Barts
(74) *Attorney, Agent, or Firm*—John J. Karasck; Joseph T. Grunkemeyer

(57) ABSTRACT

A compound having the formula $CF_3-CH(OH)-CH_2-(L)_n-CH_2-SH$ or a disulfide thereof. Each L is substituted or unsubstituted methylene, substituted or unsubstituted oxyalkylene, and alkyl-substituted or unsubstituted siloxanylene. The compound is free of carboxysilane linkages. The value of n is a positive integer. A metal surface having the group $CF_3-CH(OH)-CH_2-(L)_n-CH_2-S-$ bound thereto. A method of making $CF_3-CH(OH)-CH_2-(L)_n-CH_2-SH$ by: reacting $OHC-CH_2-(L)_n-CH_2-X$ with (trifluoromethyl)trialkylsilane to form $CF_3-CH(OH)-CH_2-(L)_n-CH_2-X$; reacting the intermediate with a thiocarbonyl compound to form an adduct; and hydrolyzing the adduct followed by protonation. X is a halogen.

29 Claims, No Drawings

TRIFLUOROMETHYLCARBINOL TERMINATED THIOLS

FIELD OF THE INVENTION

The invention is generally related to trifluoromethylcarbinol terminated thiols.

DESCRIPTION OF RELATED ART

Functionalized alkanethiols are increasingly important molecular agents for self-assembly of monomolecular coatings on a variety of metal and metal oxide surfaces. They have been employed in a variety of applications which include soft lithography, contact printing, nanocomposites fabrication, vapor and condensed phase sensors, adhesion promotion, corrosion resistance, biomolecular passivation, and nano-electronic structures. The study of unfunctionalized linear alkanethiol formations of self-assembled monolayers dates back to the work of Nuzzo and Allara (Nuzzo et al., *J. Am. Chem. Soc.* 1983, 96, 1533 (all referenced publications and patent documents are incorporated herein by reference)) on gold, and subsequent work has been the subject of several reviews (Ulman, *Chem. Rev.* 1996, 96, 1533; Schreiber, *Prog. Surf. Sci.* 2000, 65, 151; Schreiber, *J. Phys.: Condens. Matter* 2004, 16, R881). The structure of the alkane substituent and its functionalities incorporated into this substituent may determine the properties and utility of the self-assembled coating as well as influence the molecular bonding of the sulfur to the surface. A recent review of functionalized n-alkanethiols as building blocks for self-assembled monolayers more accurately depicts the synthetic strategies and methods for preparation and use of this class of alkanethiols (Witt et al., *Current Organic Chemistry* 2004, 8, 1763).

The incorporation of heterofunctionalities into the alkane thiol substituent bonded to a metal cluster is a mechanism by which selectivity is conferred to a chemiresistive sensor based on a film of such clusters. An array of such sensors with differing functionalities in the cluster shells is a method by which pattern recognition may be used for an analytical determination. Previous studies indicate the effectiveness in chemical sensors individually of terminal trifluoromethyl and terminal hydroxy (Grate et al., *Anal. Chem.* 2003, 75, 1868), but not in combination.

SUMMARY OF THE INVENTION

The invention comprises a compound comprising the formula $CF_3$—$CH(OH)$—$CH_2$—$(L)_n$—$CH_2$—$SH$ or a disulfide thereof. Each L is independently selected from substituted or unsubstituted methylene, substituted or unsubstituted oxyalkylene, and alkyl-substituted or unsubstituted siloxanylene. The compound is free of carboxysilane (Si—O—C) linkages. The value of n is a positive integer.

The invention further comprises a composition of matter comprising a metal surface having the group $CF_3$—$CH(OH)$—$CH_2$—$(L)_n$—$CH_2$—$S$— bound thereto. L and n are as defined above.

The invention further comprises a method of making a compound comprising the formula $CH_3$—$CH(OH)$—$CH_2$—$(L)_n$—$CH_2$—$SH$ comprising: reacting an aldehyde having the formula $OHC$—$CH_2$—$(L)_n$—$CH_2$—$X$ with (trifluoromethyl)trialkylsilane to form an intermediate having the formula $CF_3$—$CH(OH)$—$CH_2$—$(L)_n$—$CH_2$—$X$; reacting the intermediate with a thiocarbonyl compound to form an adduct; and hydrolyzing the adduct followed by protonation to from the compound. L and n are as defined above. X is a halogen.

DETAILED DESCRIPTION OF EXAMPLE EMBODIMENTS

In the following description, for purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well-known methods and devices are omitted so as to not obscure the description of the present invention with unnecessary detail.

Disclosed is a composition of matter identified in one embodiment as a trifluoromethylcarbinol terminated alkanethiol and a general synthetic procedure for this class of compounds. The synthesis is a three-step procedure as described below using an alkane chain of six methylene groups as an example. All three steps may proceed in remarkably good yield. The first step converts an ω-halo-α-carbinol compound, (e.g. commercailly available 6-bromo-1-hexanol), by oxidation of the alcohol to the aldehyde employing pyridinium chlorochromate (PCC). The aldehyde is then converted to the trifluoromethyl carbinol using (trifluoromethyl)trimethylsilane catalyzed with tetrabutyl ammonium fluoride. This intermediate is then converted to the trifluoromethylcarbinol terminated alkanethiol by reaction with thiourea and subsequent base catalyzed hydrolysis of the adduct (Urquhart et al., Org. Synth. Coll. Vol. III, 363 (1955)). The individual steps of this synthesis can have good to excellent yields and may be conducted on multigram or larger scales. This synthesis can be considered general to a range of alkane chain length as well as for the substitutions of other types of chains (e.g. oxyethylene, or dimethylsiloxane chains) for the alkane chain.

The compound may have a number of forms including disulfides. The general disulfide formula is $CF_3$—$CH(OH)$—$CH_2$—$(L)_n$—$CH_2$—$S$—$S$—$CH_2$—$(L)_n$—$CH_2$—$CH(OH)$—$CF_3$. The $(L)_n$ may be an alkylene group, as in $CF_3$—$CH(OH)$—$(CH_2)_n$—$SH$ and $CF_3$—$CH(OH)$—$(CH_2)_{n+2}$—$S$—$S$—$(CH_2)_{n+2}$—$CH(OH)$—$CF_3$. Suitable values for each n in this form include, but are not limited to, 1, 2, 3, 4, 5, 6, 7, 8, 9, and 10. The compound may contain one or more oxyalkylene groups such as polyoxyethylene, as in $CF_3$—$CH(OH)$—$CH_2$—$[O$—$CH_2$—$CH_2]_m$—$SH$ or $CH_3$—$CH(OH)$—$CH_2$—$[O$—$CH_2$—$CH_2]_m$—$S$—$S$—$[CH_2$—$CH_2$—$O]_m$—$CH_2$—$CH(OH)$—$CH_3$, or other oxyalkylene groups. Suitable values for the positive integer m, include, but are not limited to, 1 and 2. The compound may contain siloxanylene groups. As used herein, "siloxanylene" is a chain of alternating silicon and oxygen atoms, terminated by silicon radicals on both ends. One example is a dimethyl siloxane group as in $CF_3$—$CH(OH)$—$CH_2$—$CH_2$—$CH_2$—$[Si(CH_3)_2$—$O]_p$—$Si(CH_3)_2$—$CH_2$—$CH_2$—$CH_2$—$SH$ or $CF_3$—$CH(OH)$—$CH_2$—$CH_2$—$CH_2$—$[Si(CH_3)_2$—$O]_p$—$Si(CH_3)_2$—$CH_2$—$CH_2$—$CH_2$—$S$—$S$—$CH_2$—$CH_2$—$CH_2$—$Si(CH_3)_2$—$[O$—$Si(CH_3)_2]_p$—$CH_2$—$CH_2$—$CH_2$—$CH(OH)$—$CF_3$. The propylene groups in these examples siloxane compounds may also be other alkylene groups. Suitable values for the positive integer p, include, but are not limited to, 1 and 2. Though not so limited, the above-mentioned embodiments do not contain any adjacent oxygen atoms, as in —O—O— or adjacent silane groups, such as —Si(CH$_3$)$_2$—Si(CH$_3$)$_2$—. Combinations of methylene, oxyalkylene, and siloxanylene groups are possible.

The compound may be bound to a metal surface, such as gold. In this case, the sulfur atom is bound to the metal, covalently or otherwise, and the thiol hydrogen may be absent or remain associate with the sulfur or the compound. As used herein and in the attached claims, a S— group bound to a metal surface is defined as including both the presence and the absence of the thiol hydrogen. If the compound is a disulfide, the disulfide bond is broken for bonding to the metal.

The compound may be made, among other methods, by converting a halo aldehyde to a halo α-trifluoromethyl alcohol by reaction with a (trifluoromethyl)trialkylsilane, such as (trifluoromethyl)trimethyl silane. The halogen may be, but is not limited to, bromine, chlorine, or iodine. The aldehyde may be formed by oxidizing the corresponding alcohol with pyridinium chlorochromate (PCC), or otherwise obtained. The halo α-trifluoromethyl alcohol can then be reacted with a thiocarbonyl compound, such as thiourea, to form an adduct, which is an isothiourea hydrobromide. This adduct can have several forms in equilibrium. The adduct is then base hydrolyzed and protonated to form the trifluoromethylcarbinol terminated alkanethiol. The protonation may occur immediately with the hydrolysis in the presence of water. A mild acid may also be used for the protonation. The full synthetic scheme is shown below. The reactions typically can proceed regardless of the particular type and number of L groups used, conditions employed are typically mild.

with good signal-to-noise (i.e. 1 to 100 nA). This generally correlates with a chain length of 6 to 12 non-hydrogen atoms in the functionalized alkane or other chain substituent structure (Snow et al., "Metal-Insulator-Metal Ensemble Gold Nanocluster Vapor Sensors", in *Defense Applications of Nanomaterials*, Miziolek et al., Eds., American Chemical Society Symposium Ser. No. 891, Washington, 2004, Ch. 3). Thinner shells correlate with an instability toward agglomeration, and thicker shells correlate with too low of a conductivity. Cluster stability and solubility may be improved if there are at least two methylene groups between the thiol functional group and the balance of the substituent.

The fluoroalcohol and the thiol functional groups can confer unique properties on molecular substances which qualify them for many applications. The unique properties associated with incorporation of the fluoroalcohol functional group are a strong hydrogen bonding interaction and a proton acidity coupled with a hydrophobic character. This combination of properties makes fluoroalcohol substituted compounds surface active agents in aqueous systems and as such find applications as surfactants, wetting and dispersing agents, defoamers, phase transfer agents, polymer blend formation promoters, etc. For the detection of the organophosphorous chemical warfare agents the hydrogen bonded interaction of the fluoroalcohol alcohol with the phosphoryl group is very important for the sensitivity and selectivity of point sensors in this application. The thiol functional group is important for its coordination with metal ions and more uniquely important for its coordination with neutral metals. As such the covalently bonded adsorption of thiol function-

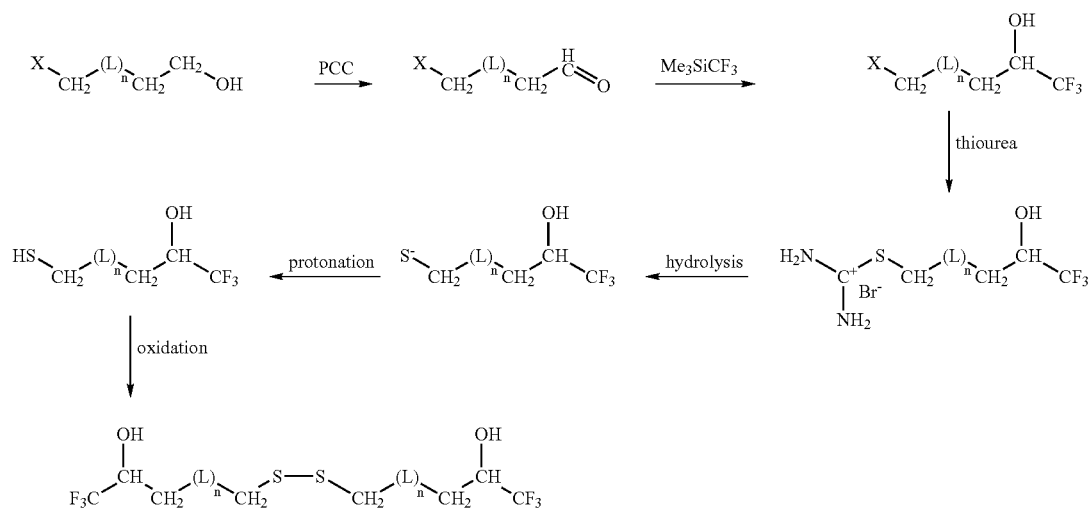

The compounds may be used in a film of encapsulated gold nanoclusters as a chemical-sensing transduction interface by a conductance modulation which is caused by the sorption and desorption of analytes into a film, as disclosed by Wohltjen et al., *Anal. Chem.* 1998, 70, 2856 and in U.S. Pat. No. 6,221,673. The magnitude of electron transport through such a film of encapsulated gold nanoclusters may be dependent on the dimensions of the gold core and the thickness of the monolayer shell (Terrill et al., *J. Am. Chem. Soc.* 1995, 117, 12537; Snow et al., *Chem. Mater.* 1998, 10, 947). For the purpose of chemical sensing, the shell thickness may fall within a thickness range where the film conductivity is sufficient for a facile current measurement alized molecules to metal surfaces has been extensively used as a metal surface treatment and finds applications that include nano- and molecular electronics, soft lithography, contact printing, nano-particulate composites, chemical sensing, corrosion resistance, adhesion promotion and electrochemistry. Numerous ω-functionalized n-alkanethiol compounds have been synthesized and investigated for properties and applications involving metal surfaces. However, none of those compounds reported to date are composed of a fluoroalcohol functional group at one end and a thiol group at the other end.

The trifluoromethylcarbinol terminated thiols have a chemistry that anticipates application for surface treatment of metals. For bulk metal surfaces the tethered fluoroalcohol functionality can impart the hydrophobic but strong hydrogen bonding character. Such a surface treatment could discourage water induced corrosion yet promote wetting and bonding with a paint. For finely divided metal particulates, particularly nano-scale, a bonded monolayer of this new compound could stabilize against irreversible agglomeration as well as making such monolayer encapsulated clusters dispersible in a variety of solvents or polymer matrices. The dimensions and character of this trifluoromethylcarbinol terminated alkanethiol may be particularly important to a chemical sensing application. In addition to the hydrogen bonded interaction with organophosphorous chemical warfare agents, the thickness of an encapsulating monomolecular layer around a nanometer-sized gold cluster may be sufficient to allow a small amount of current to pass through adjacent clusters while at the same time being highly modulated by the fluoroalcohol induced adsorption of a chemical analyte. Also, the linear chain structure of this invention can be conductive to a dense and stable packing and bonding onto the gold surface. Compared with a branch chain analog this may be an important advantage.

Having described the invention, the following examples are given to illustrate specific applications of the invention. These specific examples are not intended to limit the scope of the invention described in this application.

EXAMPLE 1

Preparation of 6-bromo-hexanal

Starting with 6-bromohexanol, oxidation to the corresponding aldehyde was performed employing a modified procedure of Hon et al., *Tetrahedron* 1998, 54, 5233. Under a positive pressure of nitrogen, 3.57 g of pyridinium chlorochromate (16.6 mmol) were combined with 25 mL of freshly distilled $CH_2Cl_2$ in a 50 mL round bottomed flask and allowed to cool at 0° C. for 30 min prior to the addition of 6-bromo-hexan-1-ol (2.00 g, 11.0 mmol). The solution was allowed to stir at 0° C. for 14 hr and then gradually warmed to rt. The solution mixture was concentrated on the rotary evaporator and then diluted with 50 mL of $Et_2O$ and passed through a pad of CELITE®. The solution that passed was combined with 3 subsequent ether washes (15 mL) and concentrated to form a clear liquid. Traces of residual solvent were removed under vacuum for 2 hr. Product was obtained (1.46 g, 74% yield), in significant purity to be used in subsequent reactions without additional purification. $^1H$ NMR: 9.74 (s, 1H), 3.38 (t, J=7, 2H), 2.45 (t, J=6, 2H), 1.87–1.80 (m, 2H), 1.65–1.58 (m, 2H), 1.49–1.42 δ (m, 2H); $^{13}C$ NMR: 202.2, 64.2, 43.6, 32.4, 27.6. 21.9 δ. Spectroscopic data correlated with that previously reported.

EXAMPLE 2

Preparation of 7-bromo-1,1,1-trifluoro-heptan-2-ol

Subsequent treatment of 6-bromo-hexanal with trimethyl(trifluoromethyl)silane in the presence of a catalytic amount of tertrabutyl ammonium fluoride (TBAF) resulted in the nucleophilic addition to the carbonyl and afforded the corresponding α-trifluoromethyl alcohol in a single step, a modification of Krishnamurti et al., *J. Org. Chem.* 1991, 56, 984. A 1.12 g sample of 6-bromo-hexanal (6.26 mmol) was combined with 8 mL freshly distilled THF and trimethyl(trifluoromethyl)silane (1.07 g, 7.51 mmol), all in a 50 mL round bottomed flask under a nitrogen atmosphere. The solution was allowed to stir for 20 min at rt and then cooled to 0° C. for 15 min prior to the addition of 20 mg of TBAF. After observation of initial yellow color formation, the ice bath was removed and solution allowed to warm to room temperature and stirred overnight. Disappearance of the carbonyl band of the starting material was confirmed by FTIR. The resulting reaction mixture was hydrolyzed upon addition of 1 mL of 5 M HCl followed by stirring at rt for 5 hr. The resulting reaction mixture was extracted with $Et_2O$ (3×75 mL), washed with $di-H_2O$ (50 mL), washed with brine (50 mL) and dried over $MgSO_4$. The resulting organic layer was concentrated to afford the desired product (1.48 g). FTIR: 3283, 2946, 2862, 1633, 1463, 1379, 1272, 1161, 1118, 841 $cm^{-1}$; $^{19}F$ NMR—79.93 δ (d, J=7, $CF_3$); $^1H$ NMR: 4.09 (t, J=6, 1H), 3.43 (t, J=7, 2H), 2.35 (bs, 1-OH), 1.91 (t, J=7, 2H), 1.87–1.41 δ (m, 6H); $^{13}C$ NMR: 121.7 (q, $CF_3$), 82.3, 34.7, 28.7, 25.4, 23.0, 20.8 δ. Anal. Calcd for $C_7H_{12}BrF_3O$: C, 33.76; H, 4.86. Found: C, 33.91; H, 4.57.

EXAMPLE 3

Preparation of 1,1,1-trifluoro-7-mercapto-heptan-2-ol

Transformation of the terminal bromide into the corresponding thiol was accomplished employing thiourea followed by base hydrolysis and subsequent protonation to afford the desired product in a 69% yield (a 49% overall yield from 6-bromohexanol). A 0.77 g sample of 7-bromo-1,1,1-trifluoro-heptan-2-ol (3.09 mmol) was combined with 3 mL absolute ehtanol and thiourea (0.26 g, 3.40 mmol) in a 15 mL round bottomed flask equipped with magnetic stir bar and reflux condenser. The reaction mixture was heated at reflux for 4 hr and allowed to cool to rt for the addition of NaOH (0.25 g, 6.18 mmol) and $di-H_2O$ (1.5 mL). The resulting solution was heated in an 80° C. oil bath for an additional 2 hr and allowed to slowly cool to rt. The resulting solution was diluted with $Et_2O$ (30 mL) and washed with $di-H_2O$ (3×10 mL). The resulting organic layer was dried over $MgSO_4$ and concentrated under reduced pressure. The impure product was distilled employing a Hickman Still to afford 0.43 g of the desired pure product. FTIR: 3395, 2930, 2860, 2557, 1459, 1389, 1274, 1170, 1128, 843, 742, 692 $cm^{-1}$; $^1H$ NMR: 3.95–3.87 (m, 1H), 3.65 (bs, 1-OH), 2.69 (t, J=6, 2H), 1.74–1.63 (m, 4H), 1.51–1.32 (m, 4H), 1.19 δ (t, J=7, 1-SH); $^{13}C$ NMR: 125.2 (q, $CF_3$), 70.2 (q, CH), 38.7, 32.3, 29.0, 27.8, 24.4 δ; $^{19}F$ NMR—80.52 δ (d, J=7, $CF_3$); Bp 106° C. (1 torr). Anal. Calcd for $C_7H_{13}F_3OS$: C, 41.57; H, 6.48. Found: C, 41.23; H, 6.71.

EXAMPLE 4 (prophetic)

Self-assembled Monolayer Film Formation

Once synthesized in free thiol or disulfide form, these α,ω-trifluoromethylcarbinol-thiol linear compounds undergo the classical self-assembled monolayer film formation onto metal surfaces [V. Chechik and C. J. M. Stirling, "Gold-Thiol Self-Assembled Monolayers" in *The Chemistry of Organic Derivatives of Gold and Silver*, S. Patai and Z. Rappoport, eds. J. Wiley & Sons, Ltd, Chichester, 1999, Chapter 15] where in this example the sulfur atom bonds to the metal surface and the trifluoromethylcarbinol moiety is oriented away from the metal surface. For planar metal substrates such as gold, silver, or platinum the self-assembly is conducted by simply contacting the clean surface of the metal with the vapor, neat liquid or a solution of the α,ω-trifluoromethylcarbinol-thiol. Conditions include temperature ranges below the boiling or decomposition points and above melting points of the α,ω-trifluoromethylcarbinol-thiol compounds or solvents in which they might be dissolved. Temperatures near ambient are preferred. As a solvent, any organic or inorganic solvent that does not chemically react with the α,ω-trifluoromethylcarbinol-thiol compound or substrate is practicable although simple organic solvents such as toluene, chloroform, ethyl acetate, and ethanol are preferred. The substrate may also be a metal cluster or rod with dimensions ranging from the nanometer to micron scale. [For recent metal nanorod and nanocluster reviews see: J. Perez-Juste, et al., "Gold Nanorods: Synthesis, Characterization and Applications", *Coordination Chem. Rev.* 249, 1870–1901, (2005) and J. H. T. Luong et al., "More Recent Progress in the Preparation of Au Nanostructures, Properties and Applications", *Anal. Lett.,* 36, 3079–3118 (2003).] With these particulate substrates, at least three self-assembly deposition processes exist: (1) direct deposition; (2) ligand exchange deposition; and (3) in situ direct synthesis. In a direct deposition, the metal clusters or rods are be performed with clean bare surfaces and simply immersed in the vapor [For general procedure, see: R. P. Andres et al., "Self-Assembly of a Two-Dimensional Superlattice of Molecularly Linked Metal Clusters", Science, 273, 1690–1693 (1996)], liquid, or solution [For general procedure, see: D. Bethell et al., "From Monolayers to Nanostructured Materials: an Organic Chemist's View of Self-Assembly", J. Electroanal. Chem., 409, 137–143 (1996)] of the α,ω-trifluoromethylcarbinol-thiol compound. In the exchange deposition the performed metal clusters or rods are coated with a monolayer of a different surface ligand and are immersed in the vapor, liquid or solution of the α,ω-trifluoromethylcarbinol-thiol compound where in an exchange reaction occurs and the surface ligand originally bonded to the metal surface is displaced by the α,ω-trifluoromethylcarbinol-thiol compound [For general procedure, see: E. E. Foos et al., "Synthesis and Characterization of Water-Soluble Gold Nanoclusters of Varied Core Size", J. Cluster Sci., 13, 543–552 (2003)]. In the in situ direct synthesis method, the clusters or rods are generated in situ with the α,ω-trifluoromethylcarbinol-thiol compound immediately present in the reaction medium, and the self-assembly occurs as the metal particulates as formed [For general procedure, see: M. Brust et al., "Synthesis of Thiol-Derivatised Gold Nanoparticles in a Two-Phase Liquid-Liquid System", J. Chem. Soc., Chem. Commun., 801–802 (1994)].

Obviously, many modifications and variations of the present invention are possible in light of the above teachings. It is therefore to be understood that the claimed invention may be practiced otherwise than as specifically described. Any reference to claim elements in the singular, e.g., using the articles "a," "an," "the," or "said" is not construed as limiting the element to the singular.

What is claimed is:

1. A compound comprising the formula CF$_3$—CH(OH)—CH$_2$—(L)$_n$—CH$_2$—SH or a disulfide thereof;
   wherein each L is independently selected from substituted or unsubstituted methylene, substituted or unsubstituted oxyalkylene, and alkyl-substituted or unsubstituted siloxanylene;
   wherein the compound is free of carboxysilane linkages; and
   wherein n is a positive integer.

2. The compound of claim 1, wherein the compound has the formula:

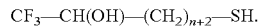
   CF$_3$—CH(OH)—(CH$_2$)$_{n+2}$—SH.

3. The compound of claim 2, wherein n is from 1 to 10.
4. The compound of claim 2, wherein n is 2 or 3.
5. The compound of claim 1, wherein the compound has the formula:

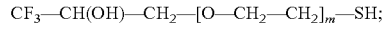
   CF$_3$—CH(OH)—CH$_2$—[O—CH$_2$—CH$_2$]$_m$—SH;

wherein m is a positive integer.

6. The compound of claim 5, wherein m is 1 or 2.
7. The compound of claim 1, wherein the compound has the formula:

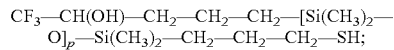
   CF$_3$—CH(OH)—CH$_2$—CH$_2$—CH$_2$—[Si(CH$_3$)$_2$—O]$_p$—Si(CH$_3$)$_2$—CH$_2$—CH$_2$—CH$_2$—SH;

wherein p is a positive integer.

8. The compound of claim 7, wherein p is 1 or 2.
9. A composition of matter comprising a metal surface having a group CF$_3$—CH(OH)—CH$_2$—(L)$_n$—CH$_2$—S— bound thereto;
   wherein each L is independently selected from substituted or unsubstituted methylene, substituted or unsubstituted oxyalkylene, and alkyl-substituted or unsubstituted siloxanylene;
   wherein the compound is free of carboxysilane linkages; and
   wherein n is a positive integer.

10. The composition of matter of claim 9, wherein the group has the formula:

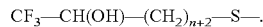
    CF$_3$—CH(OH)—(CH$_2$)$_{n+2}$—S—.

11. The composition of matter of claim 10, wherein n is from 1 to 10.
12. The composition of matter of claim 10, wherein n is 2 or 3.
13. The composition of matter of claim 9, wherein the group has the formula:

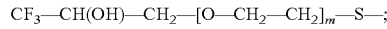
    CF$_3$—CH(OH)—CH$_2$—[O—CH$_2$—CH$_2$]$_m$—S—;

wherein m is a positive integer.

14. The composition of matter of claim 13, wherein m is 1 or 2.
15. The composition of matter of claim 9, wherein the group has the formula:

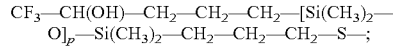
    CF$_3$—CH(OH)—CH$_2$—CH$_2$—CH$_2$—[Si(CH$_3$)$_2$—O]$_p$—Si(CH$_3$)$_2$—CH$_2$—CH$_2$—CH$_2$—S—;

wherein p is a positive integer.

16. The composition of matter of claim 15, wherein p is 1 or 2.
17. The composition of matter of claim 9, wherein the metal surface comprises gold.
18. The composition of matter of claim 17, wherein the composition comprises a film of gold nanoclusters encapsulated by the CF$_3$—CH(OH)—CH$_2$—(L)$_n$—CH$_2$—S— groups.
19. A method of making a compound comprising the formula CF$_3$—CH(OH)—CH$_2$—(L)$_n$—CH$_2$—SH comprising:
    reacting an aldehyde having the formula OHC—CH$_2$—(L)$_n$—CH$_2$—X with a (trifluoromethyl)trialkylsilane to form an intermediate having the formula CF$_3$—CH(OH)—CH$_2$—(L)$_n$—CH$_2$—X;
    reacting the intermediate with a thiocarbonyl compound to form an adduct; and hydrolyzing the adduct followed by protonation to form the compound;

wherein each L is independently selected from substituted or unsubstituted methylene, substituted or unsubstituted oxyalkylene, and alkyl-substituted or unsubstituted siloxanylene;

wherein the compound is free of carboxysilane linkages;

wherein n is a positive integer; and wherein X is a halogen.

20. The method of claim 19;

wherein the (trifluoromethyl)trialkylsilane is (trifluoromethyl)trimethylsilane; and wherein the thiocarbonyl compound is thiourea.

21. The method of claim 19, further comprising:

reacting the compound with a metal surface to bind the sulfur atom to the surface.

22. The method of claim 19, wherein the compound has the formula:

$$CF_3\text{—}CH(OH)\text{—}(CH_2)_{n+2}\text{—}SH.$$

23. The method of claim 22, wherein n is from 1 to 10.

24. The method of claim 22, wherein n is 2 or 3.

25. The method of claim 19, wherein the compound has the formula:

$$CF_3\text{—}CH(OH)\text{—}CH_2\text{—}[O\text{—}CH_2\text{—}CH_2]_m\text{—}CH_2\text{—}SH;$$

wherein m is a positive integer.

26. The method of claim 25, wherein m is 1 or 2.

27. The method of claim 19, wherein the compound has the formula:

$$CF_3\text{—}CH(OH)\text{—}CH_2\text{—}CH_2\text{—}CH_2\text{—}[Si(CH_3)_2\text{—}O]_p\text{—}Si(CH_3)_2\text{—}CH_2\text{—}CH_2\text{—}CH_2\text{—}SH;$$

wherein p is a positive integer.

28. The method of claim 27, wherein p is 1 or 2.

29. The method of claim 19, further comprising:

oxidizing the compound to a disulfide thereof.

* * * * *